United States Patent
Shie et al.

(10) Patent No.: US 8,575,578 B1
(45) Date of Patent: Nov. 5, 2013

(54) CHIP-SCALE INFRARED EMITTER PACKAGE

(71) Applicant: Oriental System Technology Inc., Hsinchu (TW)

(72) Inventors: Jin-Shown Shie, Hsinchu (TW); Chen-Tang Huang, Hsinchu (TW); Chung-Nan Chen, New Taipei (TW)

(73) Assignee: Oriental System Technology, Inc., Hsinchu (TW)

( * ) Notice: Subject to any disclaimer, the term of this patent is extended or adjusted under 35 U.S.C. 154(b) by 0 days.

(21) Appl. No.: 13/788,757

(22) Filed: Mar. 7, 2013

(30) Foreign Application Priority Data

Feb. 1, 2013 (TW) .............................. 102103998 U

(51) Int. Cl.
*G01N 21/35* (2006.01)
*G01N 21/00* (2006.01)

(52) U.S. Cl.
USPC ................. 250/504 R; 250/495.1; 250/496.1; 250/339.11; 250/339.14

(58) Field of Classification Search
USPC .................. 250/504 R, 495.1, 496.1, 339.11, 250/339.14; 338/18
See application file for complete search history.

(56) References Cited

U.S. PATENT DOCUMENTS

2013/0062738 A1* 3/2013 Chen ............................ 257/627
2013/0181808 A1* 7/2013 Chen et al. ................ 338/225 D

* cited by examiner

*Primary Examiner* — Nikita Wells
(74) *Attorney, Agent, or Firm* — Berenato & White, LLC

(57) ABSTRACT

A chip-scale infrared emitter package comprises an emitter chip and an enclosure. The emitter chip includes: a base having a central cavity; a membrane having a peripheral end, the peripheral end being isolated from a periphery of the central cavity by a loop-shaped gap; an electric resistor formed on the membrane; at least one slim supporting beam extending from the peripheral end of the membrane through the loop-shaped gap to the base; and a reflective material coated on the membrane. The enclosure has a can housing and a transparent window plate. The window plate cooperates with the can housing to define an enclosed vacuum chamber. The emitter chip is mounted in the enclosed vacuum chamber. The enclosed vacuum chamber has a pressure less than 0.01 torr.

6 Claims, 4 Drawing Sheets

CHIP-SCALE INFRARED EMITTER PACKAGE

CROSS-REFERENCE TO RELATED APPLICATIONS

This application claims priority of Taiwanese applications no. 102103998, filed on Feb. 1, 2013.

BACKGROUND OF THE INVENTION

1. Field of the Invention

This invention relates to a chip-scale infrared emitter package, more particularly to a chip-scale infrared emitter package including a membrane that is provided with an electric resistor and that is suspended in a cavity by a slim supporting beam for efficiently supplying infrared radiation.

2. Description of the Related Art

It is known that incandescent light-emitting sources can be used for generating infrared radiation for non-dispersive infrared (NDIR) gas detection. Conventional incandescent light-emitting sources include filament light bulbs and chip-type infrared emitter sources. The filament light bulbs have disadvantages, such as slow thermal response and high power consumption (about 0.6 Watt), and thus are unsuitable for battery-operated NDIR gas detection.

U.S. Pat. No. 7,989,821 illustrates a method of using semiconductor processing technology to make a sealed infrared emitter source. The infrared emitter source thus formed includes a silicon substrate having a central cavity, an emitter membrane provided with an electrical conductor of polysilicon, and a housing enclosing the silicon substrate and the emitter membrane. The emitter membrane has a peripheral end portion formed on a top surface of the silicon substrate so as to be suspended on the silicon substrate. The housing defines an enclosed space that can be filled with an inert gas or vacuum to avoid oxidation.

U.S. Patent Application Publication No. 2012/0267532 discloses an infrared emitter source that includes a silicon substrate having a central cavity, a membrane suspended on the silicon substrate, and a resistive heater formed on the membrane. Similar to the aforesaid U.S. patent, the membrane has a peripheral end portion that is formed on a top surface of the silicon substrate.

Although the sizes of the infrared emitter sources of the aforementioned U.S. patent and the U.S. patent application publication can be miniaturized, none of the aforementioned U.S. patent and the U.S. patent application publication teaches forming a loop-shaped gap between a peripheral end of the membrane and a periphery of the central cavity of the silicon substrate for thermally isolating the membrane from the silicon substrate for reducing heat loss of the membrane. In addition, none of the aforementioned U.S. patent and the U.S. patent application publication teaches that the pressure in the central cavity has a critical effect on the electro-optical efficiency (i.e., the efficiency of converting electrical power into light energy) of the infrared radiation source.

SUMMARY OF THE INVENTION

Therefore, an object of the present invention is to provide a chip-scale infrared emitter package that can overcome the aforesaid drawback associated with the prior art.

According to this invention, there is provided a chip-scale infrared emitter package that comprises an emitter chip and an enclosure. The emitter chip includes: abase having a silicon substrate, top and bottom surfaces, and a central cavity extending through the top surface and into the silicon substrate, the top and bottom surfaces being opposite to each other in a vertical direction; a membrane aligned with the central cavity in the vertical direction and having top and bottom surfaces and a peripheral end, the peripheral end being isolated from a periphery of the central cavity by a loop-shaped gap; an electric resistor formed on the top surface of the membrane for heating the membrane for generating infrared radiation; at least one slim supporting beam extending from the peripheral end of the membrane through the loop-shaped gap to the base so as to suspend the membrane in the central cavity, the slim supporting beam being reduced in dimensions from the peripheral end of the membrane so as to form a thermal bottleneck to heat conduction from the membrane to the slim supporting beam; and a reflective material coated on the bottom surface of the membrane. The enclosure has a can housing and a transparent window plate. The can housing defines a window opening. The window plate covers sealingly the window opening, and cooperates with the can housing to define an enclosed vacuum chamber which is in fluid communication with the central cavity. The emitter chip is mounted in the enclosed vacuum chamber for emitting the infrared radiation through the window plate. The enclosed vacuum chamber has a pressure less than 0.01 torr.

BRIEF DESCRIPTION OF THE DRAWINGS

In drawings which illustrate embodiments of the invention.

DETAILED DESCRIPTION OF THE PREFERRED EMBODIMENTS

Figure 1:
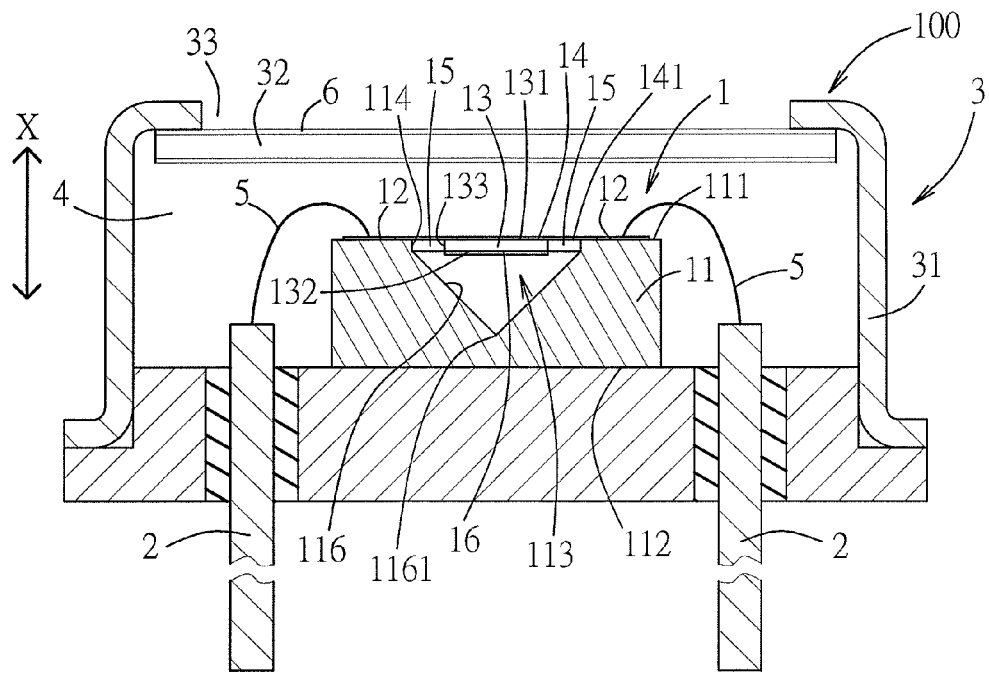
FIG. 1 is a sectional view of the first preferred embodiment of a chip-scale infrared emitter package according to the present invention.

Before the present invention is described in greater detail with reference to the accompanying preferred embodiments, it should be noted herein that like elements are denoted by the same reference numerals throughout the disclosure.

Figure 2:
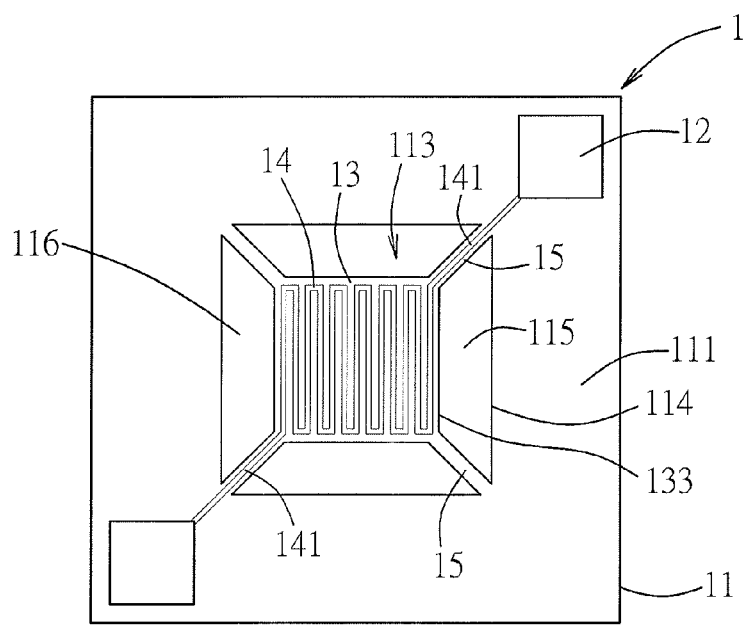
FIG. 2 is a top view of the first preferred embodiment.

FIGS. 1 and 2 illustrate the first preferred embodiment of a chip-scale infrared emitter package 100 according to the present invention. The chip-scale infrared emitter package 100 includes an emitter chip 1, a pair of conductive leads 2, an enclosure 3, and an infrared optical filter 6.

The emitter chip 1 includes: a base 11 having top and bottom surfaces 111, 112 and a central cavity 113 extending through the top surface 111 and into the base 11, the top and bottom surfaces 111, 112 being opposite to each other in a vertical direction (X), the central cavity 113 being defined by a cavity-defining wall 116 that has a tip-shaped bottom 1161 disposed above the bottom surface 112 of the base 11; a pair of conductive pads 12 formed on the top surface 111 of the base 11; a membrane 13 aligned with the central cavity 113 in the vertical direction (X) and having top and bottom surfaces 131, 132 and a peripheral end 133, the peripheral end 133 being isolated from a periphery 114 of the central cavity 113 by a loop-shaped gap 115; an electric resistor 14 formed on the top surface 131 of the membrane 13 for heating the membrane 13 for generating infrared radiation; four slim supporting beams 15 extending from the peripheral end 133 of the membrane 13 through the loop-shaped gap 115 to the base 11 so as to suspend the membrane 13 in the central cavity 113, each of the slim supporting beams 15 being reduced in dimensions from the peripheral end 133 of the membrane 13 so as to form a thermal bottleneck to heat conduction from the membrane 13 to each of the slim supporting beams 15, to reduce heat loss of the membrane 13 and to permit the membrane 13 to have a uniform temperature distribution; and a first reflective material 16 coated on the bottom surface 132 of the membrane 13.

In this embodiment, the base 11 is a silicon substrate made from a silicon wafer. The enclosure 3 has a can housing 31 and a transparent window plate 32. The can housing 31 defines a window opening 33. The window plate 32 covers sealingly the window opening 33, and cooperates with the can housing 31 to define an enclosed vacuum chamber 4 which is in fluid communication with the central cavity 113. The emitter chip 1 is mounted in the enclosed vacuum chamber 4 for emitting the infrared radiation through the window plate 32. The conductive leads 2 extend sealingly through a bottom wall of the can housing 31 and into the vacuum chamber 4 so as to be electrically and respectively connected to the conductive pads 12 through a pair of bonding wires 5. The electric resistor 14 is in the form of a meandering wire-shaped trace, and has two opposite end sections 141 disposed on and extending along upper surfaces of two respective ones of the slim supporting beams 15 to connect with the conductive pads 12, respectively.

In this embodiment, the membrane 13 and the slim supporting beams 15 are made from a silicon wafer using micro-electro-mechanical system (MEMS) technology.

The first reflective material 16 is made from a metallic material that has a high reflectivity and a low emissivity and that is preferably selected from one of silver, gold, aluminum, and platinum. In this embodiment, the first reflective material 16 is made from gold.

The infrared optical filter 6 is provided on the window plate 32, is transmissible to predetermined wavelengths of the infrared radiation (which may vary based on the gas to be detected), and is substantially untransmissible to wavelengths other than the predetermined wavelengths of the infrared radiation.

Figure 3:
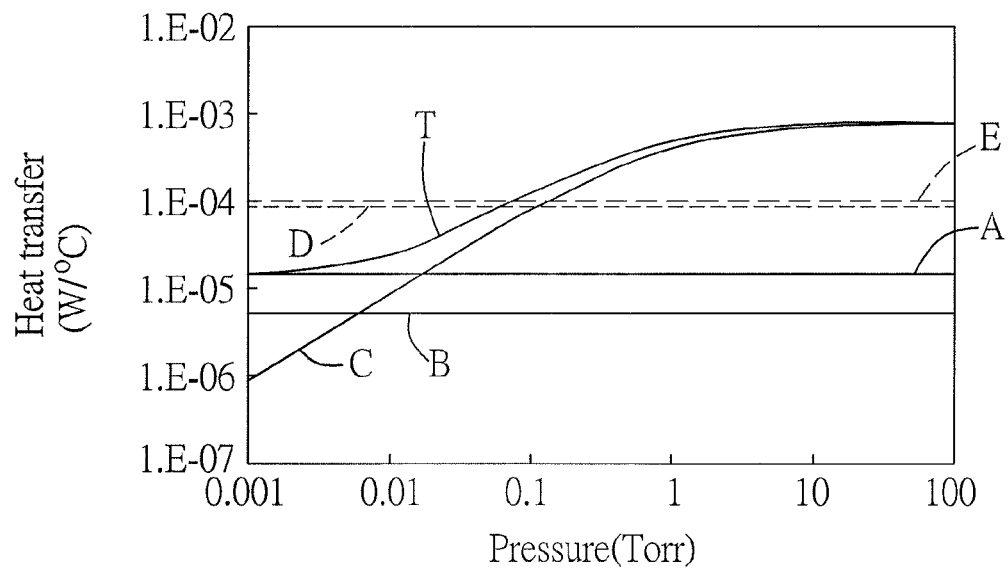
FIG. 3 is a plot showing various heat losses and a total heat loss of a membrane versus a pressure in a vacuum chamber in a can housing of the first preferred embodiment.

FIG. 3 shows various heat losses (curves A-E) and the total heat loss (curve T) of the membrane 13 versus the pressure in the vacuum chamber 4 of the first preferred embodiment. The membrane 13 for the heat loss test was operated (i.e., the membrane 13 is heated by the electric resistor 14) at a temperature of 750° C. The membrane 13 has a size of 1 mm×1 mm, and each of the slim supporting beams 15 has a length of 0.2 mm and a cross-section of 0.02 mm×0.02 mm.

The total heat loss (curve T) of the membrane 13 is a summation of a radiation heat loss (curve A, that is with the first reflective material 16 coated on the bottom surface 132 of the membrane 13), a conduction heat loss (curve B, that is with the thermal bottlenecks formed at interfaces between the membrane 13 and the slim supporting beams 15), and a convection heat loss (curve C, that is the heat loss through the air inside the vacuum chamber 4). In addition, curves D and E shown in FIG. 3 respectively represent another conduction heat loss (curve D) for the membrane 13 having a peripheral end connected entirely to the periphery of the central cavity 113 (i.e., without formation of any thermal bottleneck) and another radiation heat loss (curve E) for the membrane 13 that is without the first reflective material 16 coated on the bottom surface 132 of the membrane 13.

The Applicant found that when the pressure in the vacuum chamber 4 is greater than 0.5 torr, the convection heat loss (curve C) is much greater than the radiation heat loss of either curve A or curve E such that the effect of coating the first reflective material 16 on the bottom surface 132 of the membrane 13 on the reduction of the total heat loss of the membrane 13 is insignificant as compared to the membrane 13 that is without the first reflective material 16. Similarly, when the pressure in the vacuum chamber is greater than 0.5 torr, the convection heat loss (curve C) is much greater than the conduction heat loss (curves B and D) such that the effect of introducing the thermal bottlenecks through the slim supporting beams 15 on the reduction of the total heat loss of the membrane 13 is insignificant as compared to the membrane 13 that is not formed with the thermal bottlenecks. In addition, since the radiation heat loss of curve E (that is, without the first reflective material 16) is much greater than the conduction heat loss of curve B, the effect of introducing the thermal bottlenecks through the slim supporting beams 15 on the reduction of the total heat loss of the membrane 13 is insignificant. Hence, the Applicant found that it is necessary to lower the pressure in the vacuum chamber 4 to less than about 0.03 Torr and to form the first reflective material 16 on the bottom surface 132 of the membrane 13 so that the convection heat loss (curve C) of the membrane 13 can be reduced to a magnitude that is not greater than that of the radiation heat loss (curve A, with the first reflective material 16 coated on the bottom surface 132 of the membrane 13) and so that the introduction of the thermal bottlenecks through the slim supporting beams 15 can have a significant effect on the reduction of the total heat loss of the membrane 13. Moreover, the applicant found that the pressure in the vacuum chamber 4 is preferably less than about 0.01 Torr such that the magnitude of curve C could be close to or less than curve B. Furthermore, when the pressure in the vacuum chamber 4 reaches about 0.003 torr, further reduction of the pressure does not produce significant effect on the reduction of the total heat loss of the membrane 13.

Figure 4:
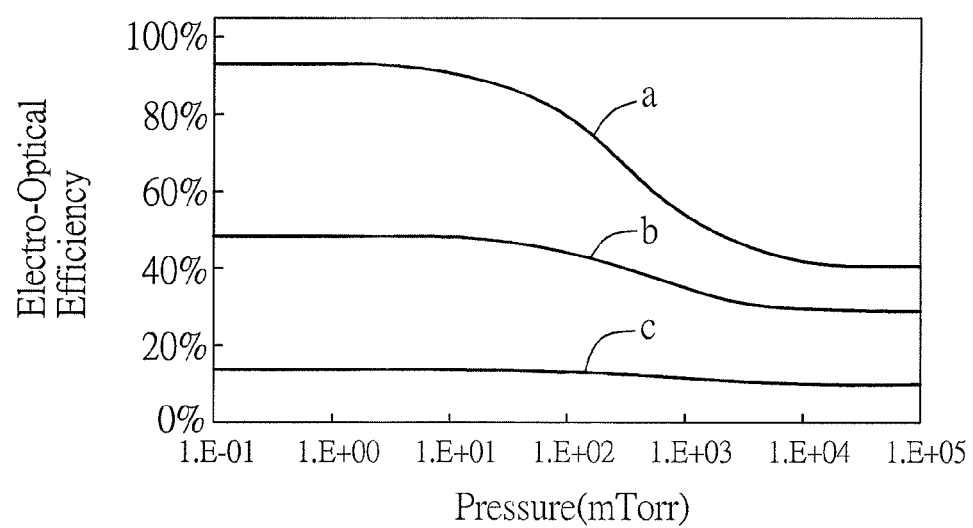
FIG. 4 is a plot for comparing the electro-optical efficiency of the first preferred embodiment with those of two comparative examples.

FIG. 4 shows a comparison of electro-optical efficiency between the first preferred embodiment (curve a) and two comparative examples (curves b and c). Curve (b) differs from the first preferred embodiment in that curve (b) is free of the first reflective material 16. Curve (c) differs from the first preferred embodiment in that curve (c) is free of the first reflective material 16 and is not formed with the thermal bottlenecks (i.e., the entire peripheral end 133 of the membrane 13 is in contact with the periphery 114 of the central cavity 113). The results show that the first preferred embodiment (curve a) can improve the electro-optical efficiency from about 12% up to about 80% as compared to curve (c) and from about 45% up to about 80% as compared to curve (b) when the pressure in the vacuum chamber 4 is about 0.1 Torr, and from about 15% up to about 92% as compared to curve (c) and from about 48% up to about 92% as compared to curve (b) when the pressure in the vacuum chamber 4 is about 0.01 Torr. In addition, the power consumption of the first preferred embodiment is about 0.15 W, which is much less than those of the conventional filament light bulbs (about 0.6 W).

Figure 5:
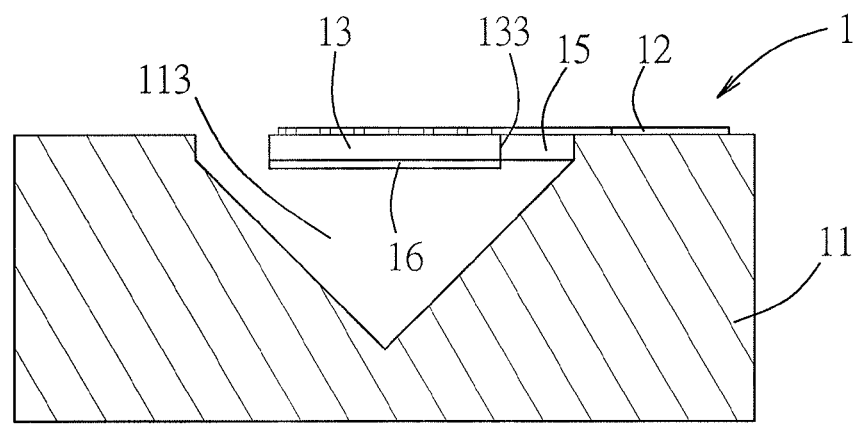
FIG. 5 is a partly sectional view of an emitter chip of the second preferred embodiment of the chip-scale infrared emitter package according to the present invention.
Figure 6:
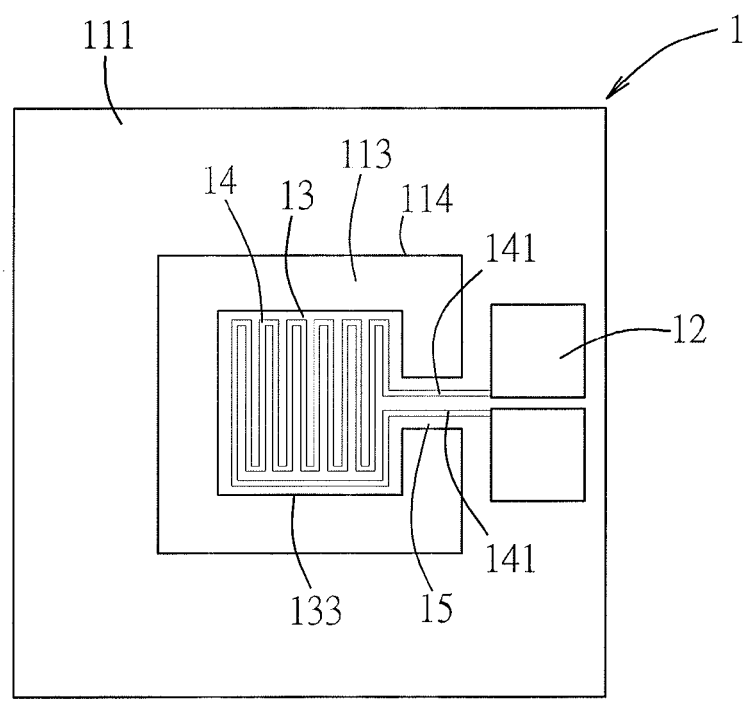
FIG. 6 is a top view of the emitter chip of the second preferred embodiment.

FIGS. 5 and 6 illustrate the second preferred embodiment of the chip-scale infrared emitter package 100 according to the present invention. The second preferred embodiment differs from the previous embodiment in that the second preferred embodiment includes one slim supporting beam 15 that interconnects the peripheral end 133 of the membrane 13 and the periphery 114 of the central cavity 113 and that both end sections 141 of the electric resistor 14 are disposed on and extend along the upper surface of the slim supporting beam 15.

Figure 7:
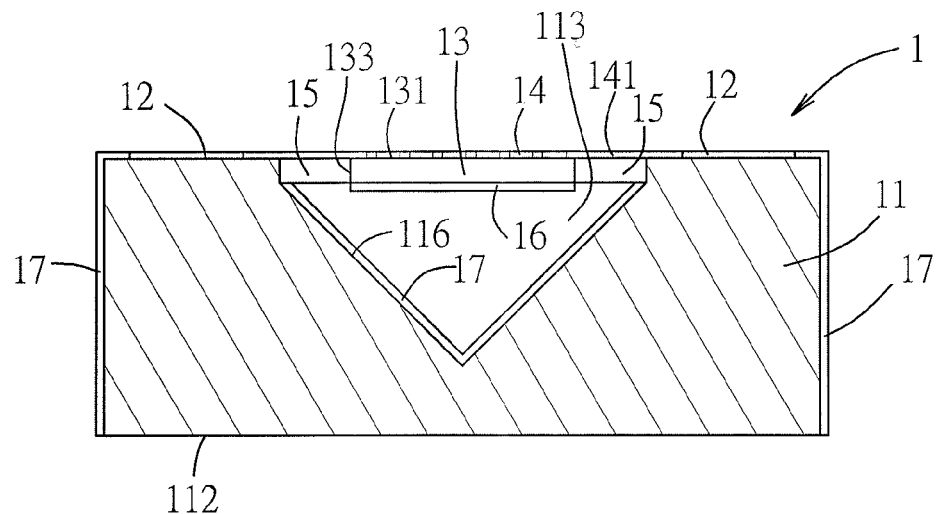
FIG. 7 is a partly sectional view of an emitter chip of the third preferred embodiment of the chip-scale infrared emitter package according to the present invention.

FIG. 7 illustrates the third preferred embodiment of the chip-scale infrared emitter package 100 according to the present invention. The third preferred embodiment differs from the first embodiment in that the third preferred embodiment further includes a second reflective material 17 formed on the cavity-defining wall 116 of the central cavity 113 and an outer peripheral surface of the base 11. The second reflective material 17 is made from a metallic material that has a high reflectivity and a low emissivity and that is preferably selected from one of silver, gold, aluminum, and platinum.

Figure 8:
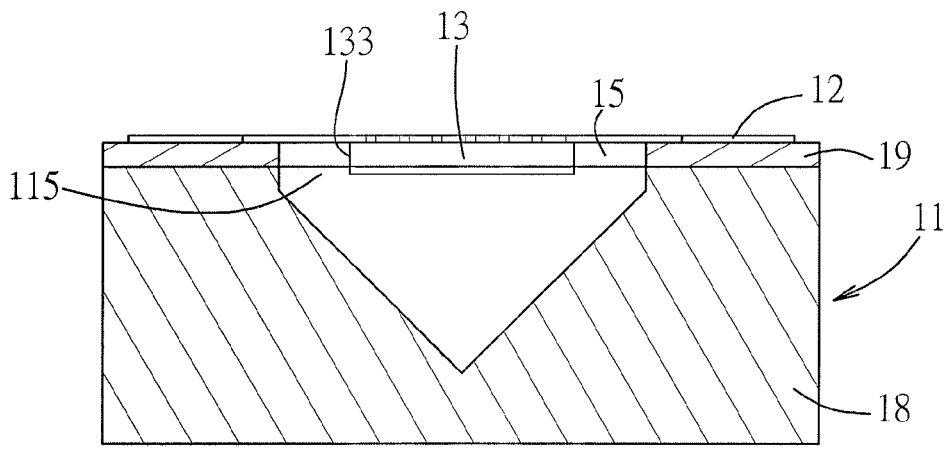
FIG. 8 is a partly sectional view of an emitter chip of the fourth preferred embodiment of the chip-scale infrared emitter package according to the present invention.

FIG. 8 illustrates the fourth preferred embodiment of the chip-scale infrared emitter package 100 according to the present invention. The fourth preferred embodiment differs from the first embodiment in that the base 11 includes a silicon substrate 18 and a spacer layer 19 formed on the silicon substrate 18. The membrane 13, the slim supporting beams 15 and the spacer layer 19 are made from silicon dioxide. The conductive pads 12 are formed on the spacer layer 19. The slim supporting beams 15 extend from the peripheral end 133 of the membrane 13 through the loop-shaped gap 115 to the spacer layer 19.

The silicon substrate 18 is made from a silicon wafer. The membrane 13 and the slim supporting beams 15 are formed using semiconductor processing techniques.

By vacuuming the vacuum chamber 4, coating the first reflective material 16 on the bottom surface 132 of the membrane 13 and forming a thermal bottleneck at the interface between the membrane 13 and each slim supporting beam 15 of the chip-scale infrared emitter package 100, the aforesaid drawback associated with the prior art can be alleviated.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A chip-scale infrared emitter package comprising:
   an emitter chip including
   a base having a silicon substrate, top and bottom surfaces, and a central cavity extending through said top surface and into said silicon substrate, said top and bottom surfaces being opposite to each other in a vertical direction, a membrane aligned with said central cavity in the vertical direction and having top and bottom surfaces and a peripheral end, said peripheral end being isolated from a periphery of said central cavity by a loop-shaped gap,
   an electric resistor formed on said top surface of said membrane for heating said membrane for generating infrared radiation,
   at least one slim supporting beam extending from said peripheral end of said membrane through said loop-shaped gap to said base so as to suspend said membrane in said central cavity, said slim supporting beam being reduced in dimensions from said peripheral end of said membrane so as to form a thermal bottleneck to heat conduction from said membrane to said slim supporting beam, and
   a first reflective material coated on said bottom surface of said membrane; and
   an enclosure having a can housing and a transparent window plate, said can housing defining a window opening, said window plate covering sealingly said window opening and cooperating with said can housing to define an enclosed vacuum chamber which is in fluid communication with said central cavity, said emitter chip being mounted in said enclosed vacuum chamber for emitting the infrared radiation through said window plate;
   wherein said enclosed vacuum chamber has a pressure less than 0.01 torr.

2. The chip-scale infrared emitter package of claim 1, wherein said central cavity is defined by a cavity-defining wall that has a bottom that is disposed above said bottom surface of said base.

3. The chip-scale infrared emitter package of claim 2, further comprising a second reflective material coated on said cavity-defining wall.

4. The chip-scale infrared emitter package of claim 1, wherein said electric resistor is in the form of a meandering wire-shaped trace, and has two opposite end sections disposed on and extending along a surface of said slim supporting beam.

5. The chip-scale infrared emitter package of claim 1, further comprising an infrared optical filter that is provided on said window plate, that is transmissible to predetermined wavelengths of the infrared radiation, and that is substantially untransmissible to wavelengths other than the predetermined wavelengths of the infrared radiation.

6. The chip-scale infrared emitter package of claim 1, wherein said first reflective material is made from a metallic material selected from silver, gold, aluminum, and platinum.

* * * * *